US009080987B2

(12) United States Patent
Faenza

(10) Patent No.: US 9,080,987 B2
(45) Date of Patent: Jul. 14, 2015

(54) OIL SOLUBLE TAGGANTS

(75) Inventor: William James Faenza, Andreas, PA (US)

(73) Assignee: ALTRIA CLIENT SERVICES, INC., Richmond, VA (US)

( * ) Notice: Subject to any disclaimer, the term of this patent is extended or adjusted under 35 U.S.C. 154(b) by 425 days.

(21) Appl. No.: 13/338,971

(22) Filed: Dec. 28, 2011

(65) Prior Publication Data
US 2012/0302474 A1    Nov. 29, 2012

Related U.S. Application Data

(60) Provisional application No. 61/490,403, filed on May 26, 2011.

(51) Int. Cl.
*C07D 209/00* (2006.01)
*C07D 207/26* (2006.01)
(Continued)

(52) U.S. Cl.
CPC  *G01N 21/94* (2013.01); *A24B 1/04* (2013.01); *A24C 1/38* (2013.01); *A24C 5/3412* (2013.01); *B07C 5/342* (2013.01); *C09K 11/00* (2013.01); *C09K 11/06* (2013.01); *C09K 11/7769* (2013.01); *C10L 1/003* (2013.01); *C10M 135/10* (2013.01); *C10M 171/007* (2013.01); *G01N 21/3563* (2013.01); *G01N 21/64* (2013.01); *G01N 21/643* (2013.01); *G01N 33/1826* (2013.01); *G01N 33/28* (2013.01); *G01N 33/2882* (2013.01); *G01N 33/2888* (2013.01); *B07C 5/3427* (2013.01); *B07C 2501/009* (2013.01); *B07C 2501/0081* (2013.01); *C09K 2211/1029* (2013.01);
(Continued)

(58) Field of Classification Search
CPC .......................... C10M 133/44; C10M 125/00
USPC ......................................................... 508/268
See application file for complete search history.

(56) References Cited

U.S. PATENT DOCUMENTS 3,417,241 A   12/1968 Davis
3,806,727 A    4/1974 Leonard et al.
(Continued)

FOREIGN PATENT DOCUMENTS

DE         20320957 U1    7/2005
DE     102011007666 A1   10/2012
(Continued)

OTHER PUBLICATIONS

International Search Report of International Application No. PCT/US2013/043172 dated Aug. 6, 2013.
(Continued)

*Primary Examiner* — James Goloboy
*Assistant Examiner* — Francis C Campanell
(74) *Attorney, Agent, or Firm* — Roberts Mlotkowski Safran & Cole, P.C.

(57) ABSTRACT

A process for detecting oil or lubricant contamination in the production of an article by adding a Stokes-shifting taggant to an oil or lubricant of a machine utilized to produce the article or a component thereof, irradiating the articles produced with a first wavelength of radiation, and monitoring the articles for emission of radiation at a second wavelength. The taggant can be in the form of a composition containing a Stokes-shifting taggant, which absorbs radiation at a first wavelength and emits radiation at a second wavelength, different from said first wavelength, dissolved or dispersed in an oil or lubricant.

16 Claims, 5 Drawing Sheets

(51) Int. Cl.

| | | |
|---|---|---|
| G01N 33/24 | (2006.01) | |
| G01N 33/00 | (2006.01) | |
| G01N 21/94 | (2006.01) | |
| A24B 1/04 | (2006.01) | |
| A24C 1/38 | (2006.01) | |
| A24C 5/34 | (2006.01) | |
| B07C 5/342 | (2006.01) | |
| C09K 11/00 | (2006.01) | |
| C10L 1/00 | (2006.01) | |
| C10M 171/00 | (2006.01) | |
| G01N 21/64 | (2006.01) | |
| G01N 33/28 | (2006.01) | |
| C09K 11/06 | (2006.01) | |
| C09K 11/77 | (2006.01) | |
| C10M 135/10 | (2006.01) | |
| G01N 21/3563 | (2014.01) | |
| G01N 21/359 | (2014.01) | |
| G01N 33/02 | (2006.01) | |
| G01N 21/84 | (2006.01) | |
| G01N 33/18 | (2006.01) | |

(52) U.S. Cl.
CPC . *C09K 2211/1044* (2013.01); *C10M 2219/044* (2013.01); *C10N 2240/56* (2013.01); *G01N 21/359* (2013.01); *G01N 33/02* (2013.01); *G01N 33/18* (2013.01); *G01N 2021/845* (2013.01); *G01N 2021/8416* (2013.01); *G01N 2201/0612* (2013.01); *G01N 2201/0697* (2013.01)

(56) References Cited

U.S. PATENT DOCUMENTS

| | | | |
|---|---|---|---|
| 3,812,349 A | 5/1974 | Gugliotta et al. | |
| 4,175,996 A | 11/1979 | Battard et al. | |
| 4,445,520 A | 5/1984 | Knight et al. | |
| 4,657,144 A | 4/1987 | Martin et al. | |
| 4,845,374 A | 7/1989 | White et al. | |
| 4,858,465 A | 8/1989 | Molina | |
| 4,971,077 A | 11/1990 | Dominguez et al. | |
| 5,048,543 A | 9/1991 | Smith | |
| 5,092,349 A | 3/1992 | Smith et al. | |
| 5,134,291 A | 7/1992 | Ruhl, Jr. et al. | |
| 5,265,732 A | 11/1993 | Long | |
| 5,462,176 A | 10/1995 | Hereford et al. | |
| 5,476,108 A | 12/1995 | Dominguez et al. | |
| 5,525,516 A * | 6/1996 | Krutak et al. | 436/56 |
| 5,554,480 A | 9/1996 | Patel et al. | |
| 5,665,538 A | 9/1997 | Slater et al. | |
| 5,715,843 A | 2/1998 | Hapke et al. | |
| 5,764,874 A | 6/1998 | White | |
| 5,807,605 A | 9/1998 | Tingey et al. | |
| 5,887,073 A | 3/1999 | Fazzari et al. | |
| 5,990,197 A | 11/1999 | Escano et al. | |
| 6,025,200 A | 2/2000 | Kaish et al. | |
| 6,060,677 A | 5/2000 | Ulrichsen et al. | |
| 6,064,032 A | 5/2000 | Voss et al. | |
| 6,135,386 A | 10/2000 | Garthaffner | |
| 6,149,719 A | 11/2000 | Houle | |
| 6,166,366 A | 12/2000 | Lewis et al. | |
| 6,380,547 B1 | 4/2002 | Gonzalez et al. | |
| 6,384,359 B1 | 5/2002 | Belcastro et al. | |
| 6,477,227 B1 | 11/2002 | Kaiser et al. | |
| 6,511,756 B1 | 1/2003 | Obuchi et al. | |
| 6,529,273 B1 | 3/2003 | Norris et al. | |
| 6,633,043 B2 | 10/2003 | Hegazi et al. | |
| 6,734,383 B1 | 5/2004 | Calcoen et al. | |
| 6,795,179 B2 | 9/2004 | Kumar | |
| 6,830,310 B2 | 12/2004 | Iu et al. | |
| 6,905,538 B2 | 6/2005 | Auslander | |
| 6,914,678 B1 | 7/2005 | Ulrichsen et al. | |
| 6,926,764 B2 | 8/2005 | Bleikolm et al. | |
| 7,153,557 B2 | 12/2006 | Rancien | |
| 7,157,611 B2 * | 1/2007 | Banavali et al. | 585/4 |
| 7,227,148 B2 | 6/2007 | Sato et al. | |
| 7,256,398 B2 | 8/2007 | Ross et al. | |
| 7,319,039 B2 | 1/2008 | Sullivan | |
| 7,378,675 B2 | 5/2008 | Ross et al. | |
| 7,391,035 B2 | 6/2008 | Kong et al. | |
| 7,488,945 B2 | 2/2009 | Li et al. | |
| 7,705,144 B2 | 4/2010 | Holmes | |
| 7,749,438 B2 | 7/2010 | Zeinali et al. | |
| 7,767,457 B2 | 8/2010 | Mun et al. | |
| 7,768,643 B1 | 8/2010 | Janssens et al. | |
| 7,800,088 B2 | 9/2010 | Ross et al. | |
| 7,842,896 B1 | 11/2010 | Calcoen et al. | |
| 7,938,124 B2 | 5/2011 | Izumiya et al. | |
| 8,415,165 B2 | 4/2013 | Liang et al. | |
| 8,641,933 B2 | 2/2014 | Purdy et al. | |
| 2001/0045378 A1 | 11/2001 | Charles et al. | |
| 2002/0094058 A1 | 7/2002 | Kaiser et al. | |
| 2002/0097833 A1 | 7/2002 | Kaiser et al. | |
| 2003/0034282 A1 | 2/2003 | Safai | |
| 2003/0058990 A1 | 3/2003 | Kaiser et al. | |
| 2003/0097833 A1 | 5/2003 | Ingram et al. | |
| 2003/0129283 A1 | 7/2003 | Martinez Carballido | |
| 2003/0141459 A1 | 7/2003 | Hegazi et al. | |
| 2003/0183326 A1 | 10/2003 | O'Connor | |
| 2003/0194052 A1 | 10/2003 | Price et al. | |
| 2005/0031838 A1 | 2/2005 | Lagunowich et al. | |
| 2005/0092336 A1 | 5/2005 | Zielke et al. | |
| 2005/0276906 A1 | 12/2005 | Metzger | |
| 2006/0016735 A1 | 1/2006 | Ito et al. | |
| 2006/0118741 A1 | 6/2006 | Ross et al. | |
| 2006/0131518 A1 | 6/2006 | Ross et al. | |
| 2006/0246020 A1 | 11/2006 | Cole et al. | |
| 2006/0262318 A1 | 11/2006 | Sullivan | |
| 2006/0291872 A1 | 12/2006 | Mei et al. | |
| 2007/0023715 A1 | 2/2007 | Ross et al. | |
| 2007/0048761 A1 | 3/2007 | Reep et al. | |
| 2007/0084269 A1 * | 4/2007 | Quest et al. | 73/40.7 |
| 2007/0187617 A1 | 8/2007 | Kong et al. | |
| 2008/0030712 A1 | 2/2008 | Tokhtuev et al. | |
| 2009/0047531 A1 | 2/2009 | Bartley et al. | |
| 2009/0097833 A1 | 4/2009 | Imada | |
| 2009/0185182 A1 | 7/2009 | Kim et al. | |
| 2009/0280341 A1 | 11/2009 | Maruichi et al. | |
| 2009/0321623 A1 | 12/2009 | Ross et al. | |
| 2010/0080456 A1 | 4/2010 | Paul et al. | |
| 2010/0219377 A1 | 9/2010 | Ebert | |
| 2010/0224795 A1 | 9/2010 | Cole et al. | |
| 2010/0226861 A1 | 9/2010 | Cole et al. | |
| 2010/0233447 A1 | 9/2010 | Campbell | |
| 2010/0290040 A1 | 11/2010 | Berghmans | |
| 2011/0141272 A1 | 6/2011 | Uto et al. | |
| 2011/0151576 A1 | 6/2011 | Perfect et al. | |
| 2011/0216190 A1 | 9/2011 | Shimazu et al. | |
| 2012/0104278 A1 | 5/2012 | Downing et al. | |
| 2012/0302474 A1 | 11/2012 | Faenza | |
| 2013/0082173 A1 | 4/2013 | Cadieux et al. | |
| 2013/0188170 A1 | 7/2013 | Wilkins | |

FOREIGN PATENT DOCUMENTS

| | | |
|---|---|---|
| EP | 0146299 A1 | 6/1985 |
| EP | 0223446 A2 | 5/1987 |
| EP | 657028 B1 | 6/1995 |
| EP | 0897762 A2 | 2/1999 |
| GB | 2091416 | 7/1982 |
| WO | 9117265 A1 | 11/1991 |
| WO | 9800243 A1 | 1/1998 |
| WO | 9957417 A2 | 11/1999 |
| WO | 0125747 A2 | 4/2001 |
| WO | 0125748 A2 | 4/2001 |
| WO | 0125764 A1 | 4/2001 |
| WO | 0125766 A1 | 4/2001 |
| WO | 0125767 A1 | 4/2001 |
| WO | 0125820 A2 | 4/2001 |
| WO | 02068945 A1 | 9/2002 |
| WO | 2008049515 A2 | 5/2008 |
| WO | 2010/007390 A2 | 1/2010 |

(56) References Cited

FOREIGN PATENT DOCUMENTS

| WO | 2012030988 A1 | 3/2012 |
|---|---|---|
| WO | 2012050844 A1 | 4/2012 |
| WO | 2012162701 A4 | 5/2013 |

OTHER PUBLICATIONS

Victoria B. Rodriguez et al., Encapsulation and Stabilization of Indocyanine Green within Poly(Styrene-Alt-Maleic Anhydride) Block-Poly(Styrene) Micelles for Near-Infrared Imaging, Journal of Biomedical Optics; Jan. 30, 2008, vol. 13 No. 1, pp. 14025-1-140025-10; XP002664215.

International Search Report of International Application No. PCT/US2012/039870 dated Jan. 14, 2013.

International Search Report of International Application No. PCT/US2014/026556 dated Aug. 5, 2014.

\* cited by examiner

OIL SOLUBLE TAGGANTS

RELATED APPLICATION

This patent application claims priority to U.S. Provisional Application Ser. No. 61/490,403, filed on May 26, 2011, the contents of which are hereby incorporated by reference in their entirety.

FIELD

Disclosed herein is a light wavelength converting material for taggant applications and quantitative diagnostics.
Environment In the processing and packaging of various consumer products, oils, greases and lubricants may come into contact with the product.

Typically, lubricants can come into contact with consumer products due to leakage of lubricants through gaskets or seals, from sliding mechanisms, from drum systems, from gear boxes, from pumps, from sealed rolling bearing units, from chains and belts, and the like. For example, lubricants are used in a variety of machines commonly used in the preparation and packaging of produce for market.

Since lubricants of similar compositions are used throughout the various stages of produce treatment and packaging, it is often difficult for the manufacturer to locate the source of a particular lubricant. As such, the manufacturer is forced to conduct a time consuming search for the source of the lubricant which is lowering the quality of the manufactured products.

One possible way to detect the presence of undesired lubricants would be to add a taggant to the lubricant that could be readily detected on-line and at production speeds. However, suitable oil soluble taggants are not known to exist.

Therefore, it would be advantageous if an oil-soluble taggant could be developed that would enable inspection to be conducted on-line, in real time, during the production process.

SUMMARY

In one form, disclosed is a fluorescent taggant composition, comprising a Stokes-shifting taggant, which absorbs radiation at a first wavelength and emits radiation at a second wavelength, different from said first wavelength; and an oil or lubricant.

In another form, disclosed is a taggant composition, comprising an oil-soluble fluorescent taggant and an oil or lubricant.

In yet another form, disclosed is a compound comprising a tetrabutylammonium chloride complex of Indocyanine Green (ICG).

BRIEF DESCRIPTION OF THE DRAWINGS

The forms disclosed herein are illustrated by way of example, and not by way of limitation, in the figures of the accompanying drawings and in which like reference numerals refer to similar elements and in which.

DETAILED DESCRIPTION

Figure 1:
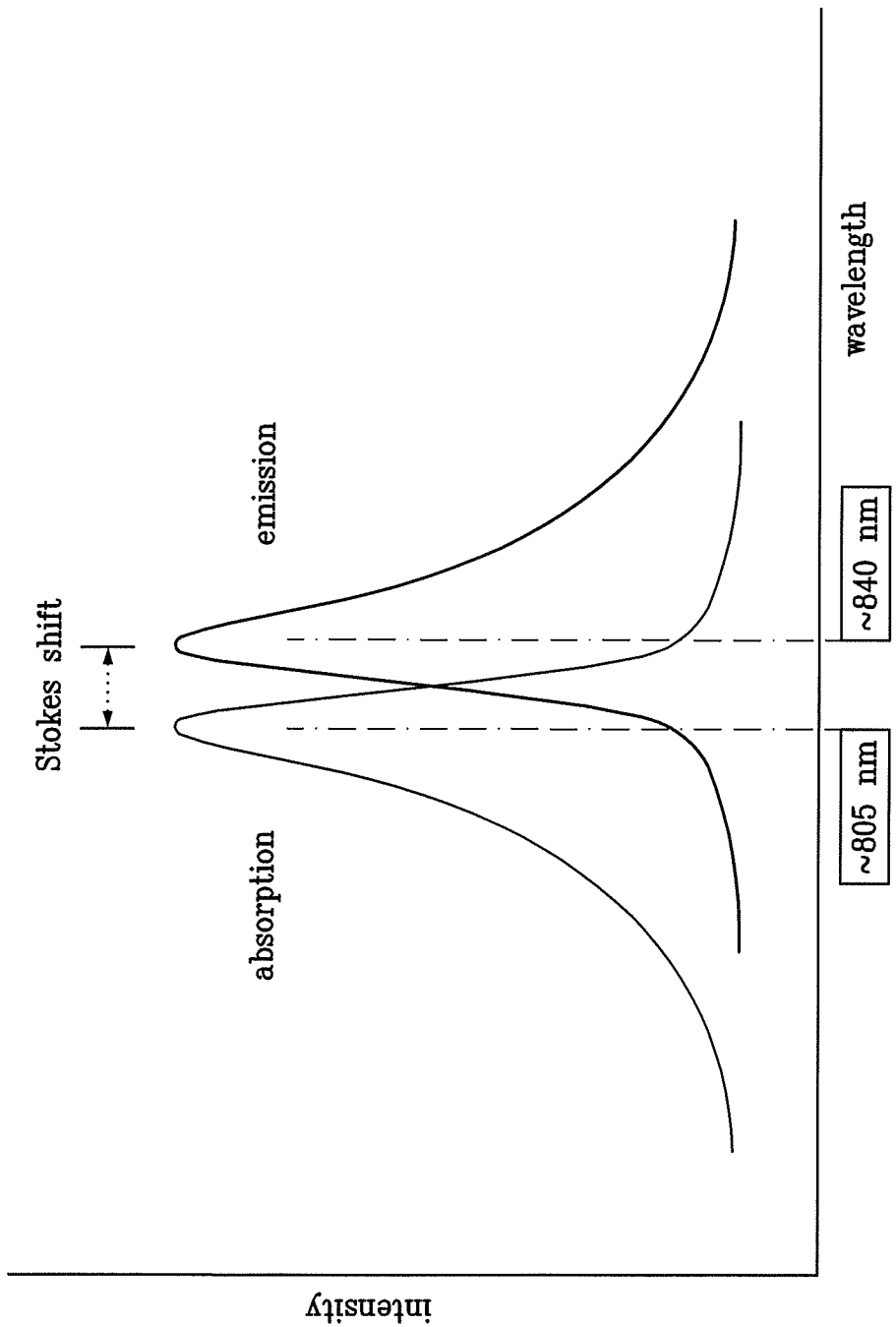
FIG. 1 is a representation of the infrared absorption and emission peaks of the Indocyanine Green (ICG) complex taggant, illustrating the Stokes-shift.

Various aspects will now be described with reference to specific forms selected for purposes of illustration. It will be appreciated that the spirit and scope of the apparatus, system and methods disclosed herein are not limited to the selected forms. Moreover, it is to be noted that the figures provided herein are not drawn to any particular proportion or scale, and that many variations can be made to the illustrated forms. Reference is now made to FIGS. 1-5, wherein like numerals are used to designate like elements throughout.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

Provided are new oil soluble, light wavelength-converting, preferably upconverting, compositions for taggant applications and quantitative diagnostics in connection with lubricants, such as by way of non-limiting example, the detection of errant lubricants on product that comes into contact with lubricated machinery. Other taggant applications are contemplated, including, but not limited to, anti-counterfeiting, brand protection, or verification that a machine contains a correct lubricant, and other possible applications. A detection system enables the development of near real time, low cost, compact, portable and highly sensitive detection, monitoring and diagnostics of modifications to manufacturing process systems in real world environments. It is the unique process (e.g. the conversion of visible light to infrared light, infrared to visible light and the upconversion of infrared to higher energy infrared) that enables high sensitivity detection against almost any sample or environmental background.

Using the system, theoretical particle detection ($10^{23}$ mol) of molecules added to analytic mixtures can be achieved through the use of on-line verification methods and even handheld detection applications. Detection sensitivity of $10^{-20}$ mol is possible in a variety of detection schemes, and even direct visual detection of $10^{-14}$ mol sensitivity has been demonstrated using a hand held 3.0 to 9.0 volt laser diode system against backgrounds of various colors and compositions. The narrow emission bandwidths and small particle size of these materials enable the simultaneous detection of multiple analytes (i.e. multiplexed assays).

According to the present invention, a detectable taggant compound is added to the various lubricants used in manufacturing and processing machinery, and advantageously taggant compounds having different characteristics are added into the lubricants at different processing locations, such that detection of one or more of these taggant compounds can enable rapid identification of the location of the source of lubricant contamination in the manufactured product.

Advantageously, the taggant compound is one which is detectable by fluorescence when it is exposed to particular wavelengths of light. In particular, a suitable taggant is one which absorbs energy at one wavelength and fluoresces/emits at a different wavelength. Such materials are well-known in the art as Stokes-shifting materials, and have recently found increasing use in inks for security marking of documents, such as banknotes and the like, to render such documents less susceptible to counterfeiting or copying.

However, most conventional Stokes-shifting and anti-Stokes shifting materials are composed of inorganic compounds, such as doped rare earth metal particles as described in U.S. Published Patent Application No. 2010/0219377, which are insoluble in lubricants. It would be advantageous if taggant compounds could be formulated to be soluble or dispersible in oils or lubricants.

According to the present invention, the taggant may be an organic compound comprised of purified crystals from naturally occurring chlorophyll. Suitable naturally-occurring chlorophyll crystals include Chlorophyll A (CAS number 1406-65-1) and Chlorophyll B (CAS number 519-62-0). These taggants are known as being down-converting or fluorescent, and are sensitive to excitation at a particular narrow bandwidth of IR light (680 nanometers). The taggant emits light at a different wavelength (715 nanometers). A similar compound may be a benze-indolium perchlorate or a benze-indolium tosolyate. Such materials absorb at around 670 nanometers and emit at a wavelength of about 713 nanometers. The chemical structure for Chlorophyll A is provided below.

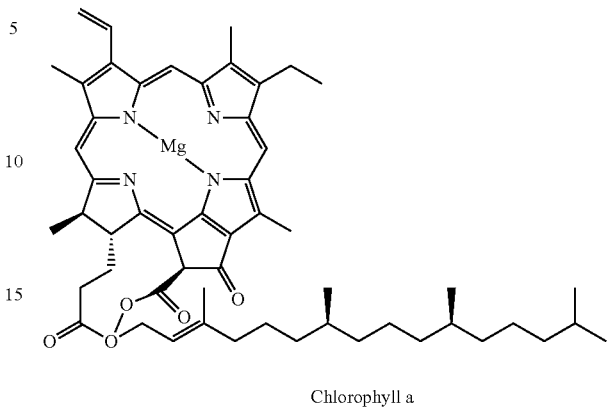

Chlorophyll a

Since this compound is an organic chemical, it is readily dissolved in oils and lubricants.

In another form, an oil-soluble fluorescent material has been developed based on Indocyanine Green (ICG), the chemical structure of which is provided below.

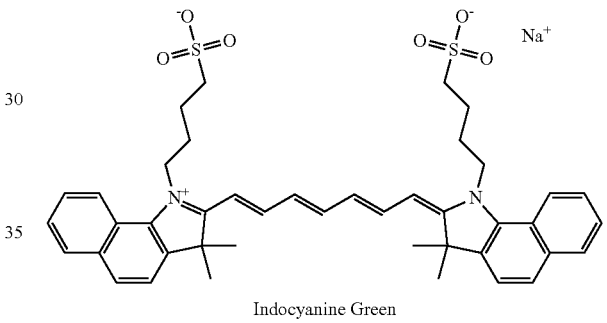

Indocyanine Green

ICG is sodium 4-[2-[(1E,3E,5E,7Z)-7-[1,1-dimethyl-3-(4-sulfonatobutyl)-benzo[e]indol-2-ylidene]hepta-1,3,5-trienyl]-1,1-dimethyl-benzo[e]indol-3-ium-3-yl]butane-1-sulfonate, an infrared fluorescing compound currently used in the medical industry for imaging cells and blood flows in the human body, which in its conventional form is water-soluble.

The newly developed taggant is an ICG-complex available from Persis Science LLC, Andreas Pa. The chemical structure for a tetrabutylammonium chloride complexation of ICG is provided below and analytical structural information is provided in FIG. 5.

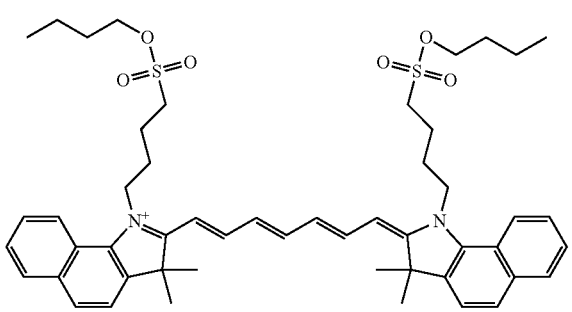 [SMILES: CCCCOS(=O)(=O)CCCCN1/C(=C/C=C/C=C/C=C/C2=[N+](CCCCS(=O)(=O)OCCCC)c3c(ccc4ccccc34)C2(C)C)C(C)(C)c2ccc3ccccc3c21]

The new ICG-complex is sensitive to a particular narrow absorption band of IR light between about 760 to about 810 nanometers (FIG. 3), and emits light at a different band between about 810 to about 840 nanometers (FIG. 4), with discrete absorbance peaks at about 785 nanometers (FIGS. 4) and 805 nanometers (FIG. 1), and a discrete emission peak at about 840 nanometers (FIG. 1).

The ICG complex can be added to oils or lubricants in the amounts of approximately 1 ppb to 5%, preferably a range of 1 ppm to 2000 ppm, based on the weight of the lubricant.

Figure 2:
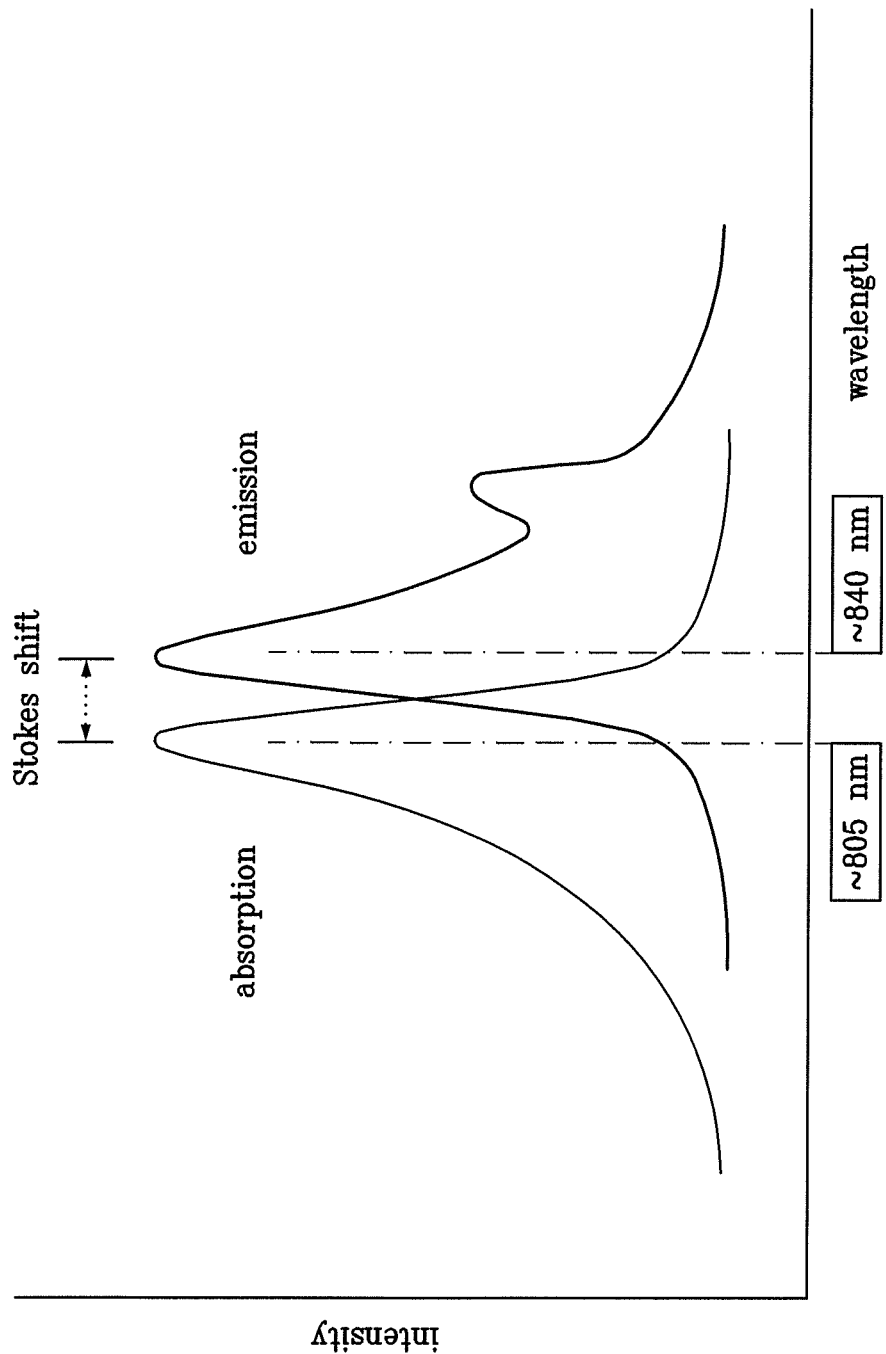
FIG. 2 is a representation of the infrared absorption and emission peaks of a modified ICG-complex, illustrating a secondary emission peak.
Figure 3:
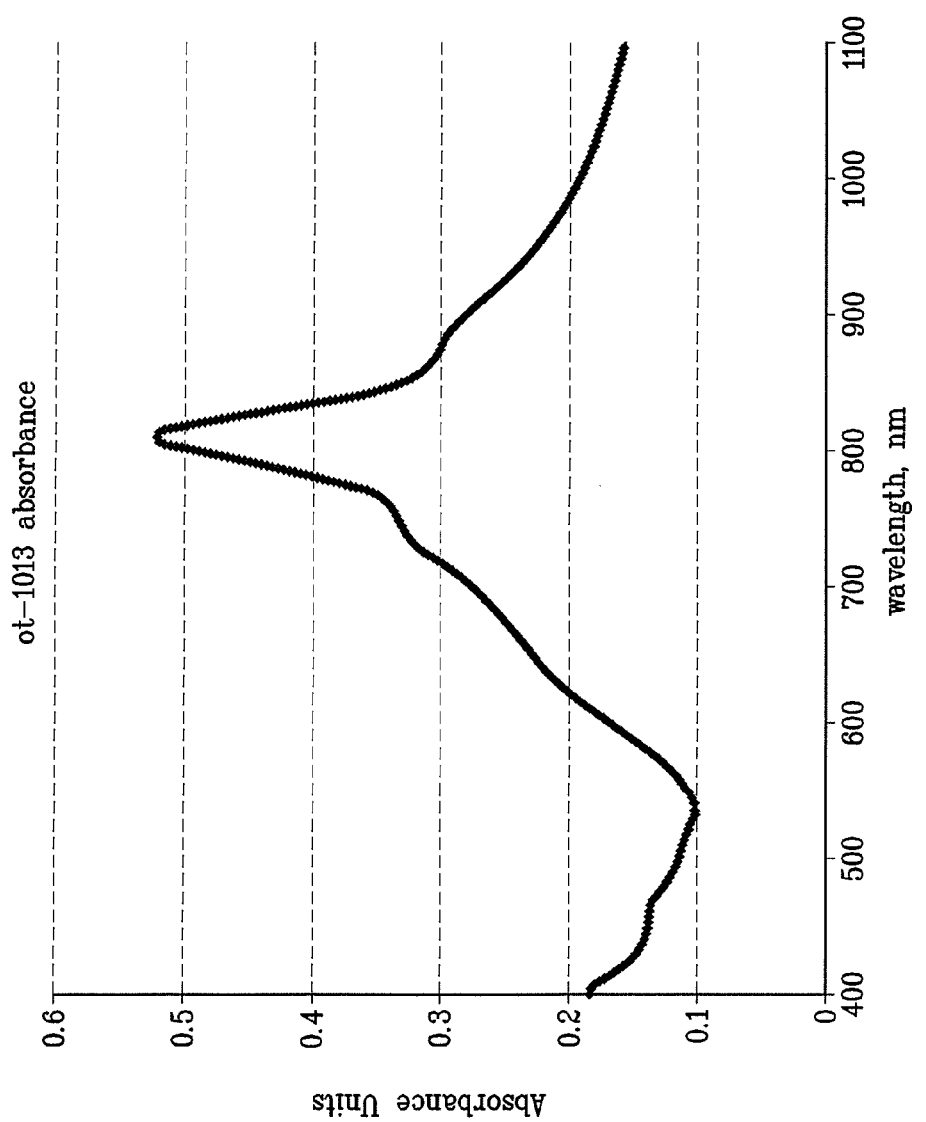
FIG. 3 is a representation of the infrared absorption peak for the modified ICG-complex of Example 1.
Figure 4:
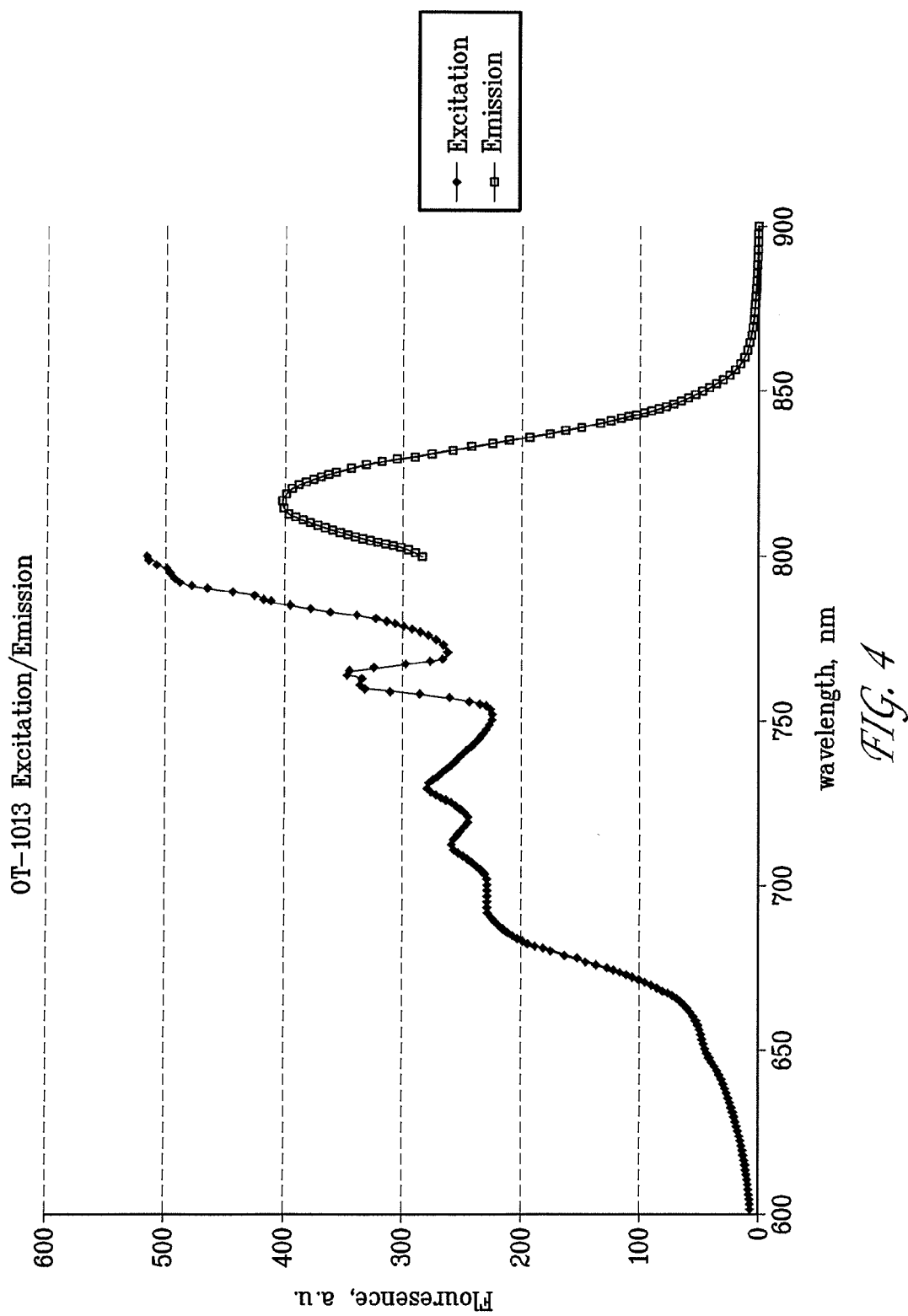
FIG. 4 is a representation of the infrared excitation and emission peaks for the modified ICG-complex of Example 1.
Figure 5:
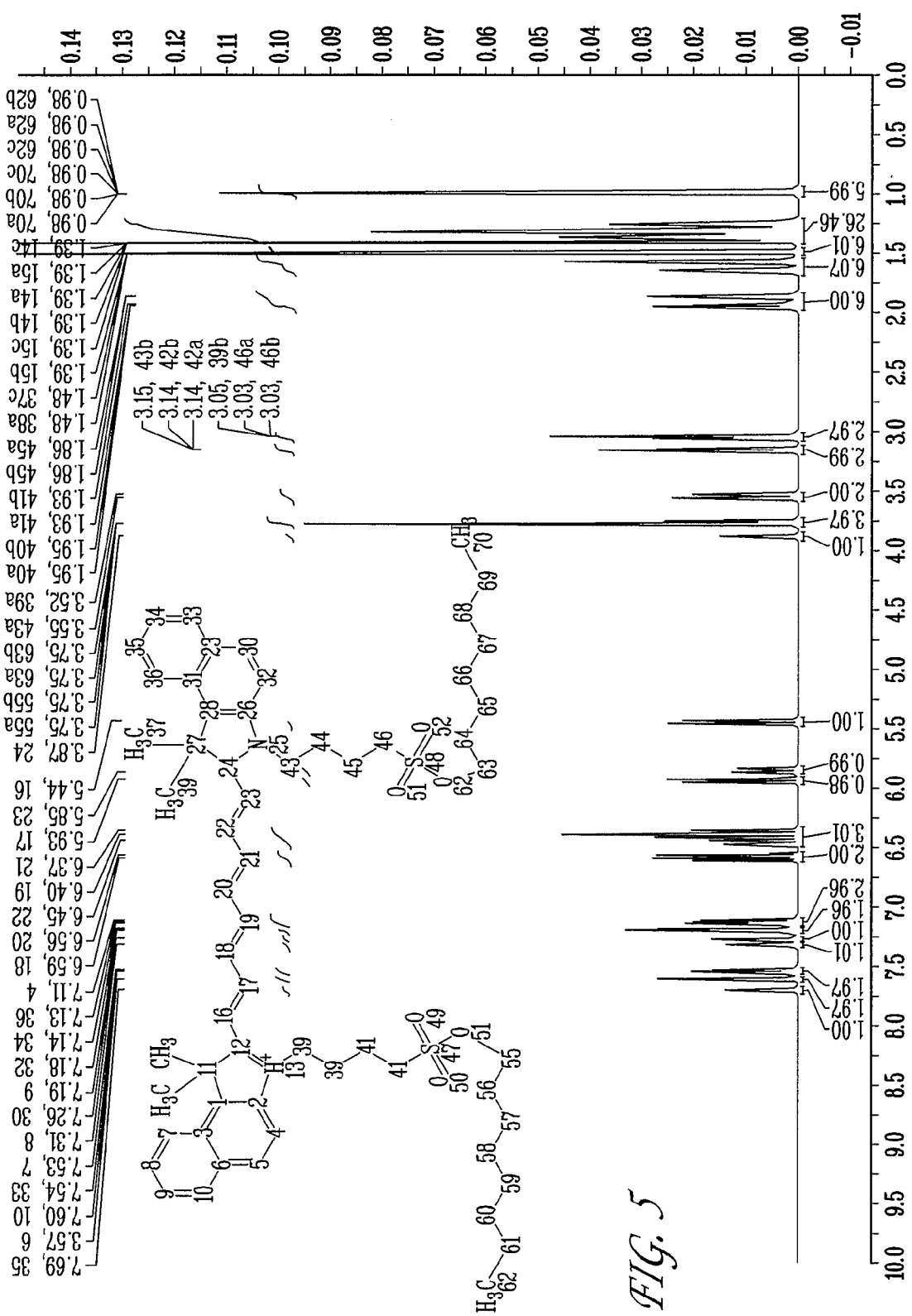
FIG. 5 is an H-nuclear magnetic resonance scan of the ICG-complex according to this invention.

Additionally, the nature of the ICG complexing agent can be modified to impart one or more secondary NIR reflectance wavelengths adjacent to the major emission peak at 840 nanometers. By utilizing such variations in the complexing agent, and adding differently complexed ICG compounds in lubricants at differing locations in the overall process, a single detector can be located at the end of the process, and when contamination is detected, the contaminated product can be removed from the process and further analyzed for said secondary NIR reflectance peaks, to determine the location of the source of contamination. FIG. 2 is an illustration of the absorption and emission peaks of a modified ICG-complex, showing a secondary emission peak of a longer wavelength on the shoulder of the primary emission peak.

The detection system of the present invention can be used in many processes and for consumer products which are susceptible to lubricant contamination during the manufacturing process, such as for example in the growing, collection, processing and/or packaging of packaged consumer goods, such as food products, beverages, tipped and non-tipped cigars, cigarillos, snus and other smokeless tobacco products, smoking articles, electronic cigarettes, distilled products, pharmaceuticals, frozen foods and other comestibles, and the like. Further applications could include clothing, furniture, finished wood or lumber or any other manufactured or packaged product wherein an absence of oil spotting is desired.

The taggant can be added to process machinery lubricants in minor amounts, so as to obtain ultimate concentrations in the oil/lubricant as low as between about 10 ppm and 100 ppm, typically at a concentration of about 50 ppm. At these taggant concentration levels the detection system can detect as little as 10 microliters of oil, or even as little as 1 microliter of tagged oil.

However, in order to provide for easier treatment of oils or lubricants already in place within various machines, it can be more convenient to formulate a master batch of the taggant in any particular oil, wherein the taggant is mixed at higher concentrations in the base oil/lubricant, such as from about 0.1 to about 5 wt % taggant, or even from about 0.2 to about 2 wt % taggant, in a balance of the base oil/lubricant. A portion of such tagged master batch is then easily transported and added to oils/lubricants which are already in place in the machines to be treated, for example by adding a small amount of the tagged master batch to the oil sump of the machine.

When the taggant is not an oil-soluble taggant, such as when it is an inorganic particle, an optional surfactant or dispersant additive can be added in an amount effective to facilitate dispersion of the taggant particles in the base oil. Such surfactants/dispersants are well-known in the art and their identities need not be repeated herein.

Specific forms will now be described further by way of example. While the following examples demonstrate certain forms of the subject matter disclosed herein, they are not to be interpreted as limiting the scope thereof, but rather as contributing to a complete description.

EXAMPLES

Example 1

500 mg of complexed ICG (Product No. OT-1013, available from Persis Science LLC of Andreas Pa.) is dispersed into 1.0 kg of Klüberoil 68 using a speedmixer. Klüberoil 68 is available from Klüber Lubrication North America L.P., Londonderry, N.H. The material is mixed for 10.0 minutes at a speed of 2100 RPM. The resulting master batch concentrate is slowly added to an additional 100.0 kg of Kluberoil 68 while stirring under high speed dispersion. A sample of the material is placed into a Shimadzu 5301 Fluorometer and the excitation and emission spectrographs are recorded. When excited at a wavelength of 785, a strong infrared emission is noted from 810 nanometers to 960 nanometers. See FIG. 3 for a representation of the infrared absorption peak for the ICG-complex of Example 1 and FIG. 4 for a representation of the infrared excitation and emission peaks for the ICG-complex of Example 1.

Example 2

The above example is modified slightly using a tetrabutylammonium bromide complexation of an Infrared dye IR830, available from Sigma-Aldrich of St. Louis, Mo. After mixing, it is noted that the material will produce fluorescence around 833 nanometers when excited with approximately 0.5 mW of 785 light.

Example 3

Upconverting nanoparticles, MED C-19 ($Yb_2O_3$:$Er^{3+}$), were obtained from Persis Science, LLC in a slurry format in DMSO. The DMSO was dialyzed from the aqueous phase leaving the particles in aqueous phase. The particles were dried and dispersed into Kluberoil 68 using a Speedmixer. The dispersion was measured optically using a Spex Fluorolog-3. The oil suspension was excited at 970 nm and the detection occurred in the visible from 400 to 700 nm to determine the presence of the tagged oil.

Example 4

0.5 wt % of a europium chelate, available from Honeywell Corporation under the trade name of CD-335, was incorporated into 99.5 wt % of Lubriplate 220 oil using a horizontal media mill. Adequate detection was achieved using UV LED's at a wavelength of 363 nm and an APD detector with a 600 nm-700 nm notch filter.

Example 5

1.0 wt % of an infrared absorbing dithiolene dye commercially available from Epolin, Inc—358 Adams St. Newark N.J. 07105, was dissolved via mixing with 99 parts of Kluber Oil 220 under nitrogen with a stir bar for 5 hours. The resulting mixture was analyzed for infrared absorption. The absorption occurred from 800 nm to 1200 nm with a peak at around 1060 nm. The detection was achieved by contrast imaging with a Cognex In-Sight vision system and using a Monster LED light system with a wavelength of 850 nm. A Midwest optical filter 850 bandpass was used to isolate the absorption.

While the present invention has been described and illustrated by reference to particular forms, those of ordinary skill in the art will appreciate that the invention lends itself to variations not necessarily illustrated herein. For this reason, then, reference should be made solely to the appended claims for purposes of determining the true scope of the present invention.

I claim:

1. A fluorescent taggant composition, comprising:
a Stokes-shifting taggant comprising the following chemical structure:

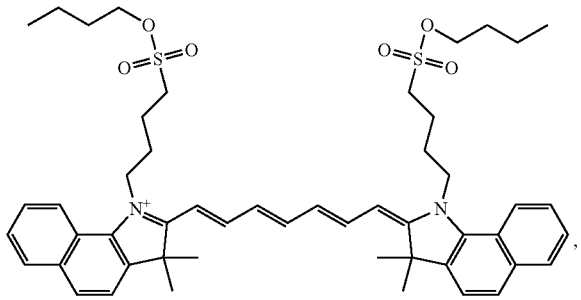 [SMILES: CCCCOS(=O)(=O)CCCCN1/C(=C/C=C/C=C/C=C/C2=[N+](CCCCS(=O)(=O)OCCCC)c3c(ccc4ccccc34)C2(C)C)C(C)(C)c2ccc3ccccc3c21]

which absorbs radiation at a first wavelength and emits radiation at a second wavelength, different from said first wavelength; and
an oil or lubricant.

2. The composition of claim 1, wherein said first wavelength is about 760 to about 810 nanometers and said second wavelength is about 810 nanometers to about 960 nanometers.

3. The composition of claim 1, wherein the Stokes-shifting taggant is present in a minor amount and the oil or lubricant is present in a major amount.

4. The composition of claim 1, wherein the Stokes-shifting taggant is present in an amount of from about 0.1 to about 5 wt % in the oil or lubricant.

5. The composition of claim 1, wherein the Stokes-shifting taggant is an oil-soluble taggant and is dissolved in said oil or lubricant.

6. The composition of claim 1, wherein the Stokes-shifting taggant is an Indocyanine Green complex.

7. The composition of claim 1, wherein the Stokes-shifting taggant is an oil-dispersible taggant and is dispersed in said oil or lubricant, and optionally further comprising a surfactant or dispersant additive.

8. The composition of claim 1, wherein the Stokes-shifting taggant is added to said oils or lubricants at a concentration of between about 10 ppm and about 100 ppm.

9. A taggant composition, comprising: a oil-soluble or dispersible fluorescent taggant comprising the following chemical structure:

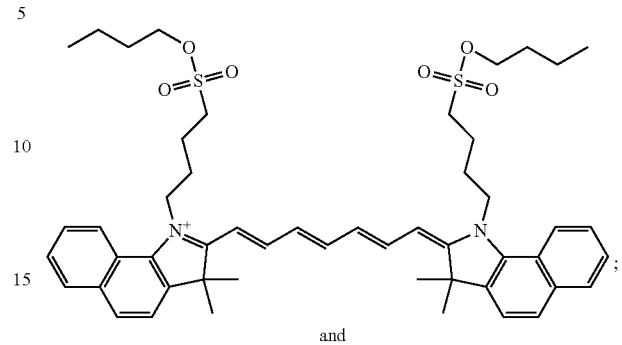

and
an oil or lubricant.

10. The taggant composition of claim 9, wherein the taggant is a Stokes-shifting taggant, which absorbs infrared radiation at a first wavelength and emits infrared radiation at a second wavelength, different from said first wavelength.

11. The taggant composition of claim 10, wherein said first wavelength is about 760 to about 810 nanometers and said second wavelength is about 810 nanometers to about 960 nanometers.

12. The taggant composition of claim 11, wherein the Stokes-shifting taggant is present in a minor amount and the oil or lubricant is present in a major amount.

13. The taggant composition of claim 12, wherein the Stokes-shifting taggant is present in an amount of from about 0.1 to about 5 wt % in the oil or lubricant.

14. The taggant composition of claim 10, wherein the Stokes-shifting taggant is an oil-soluble taggant and is dissolved in said oil or lubricant.

15. The taggant composition of claim 10, wherein the Stokes-shifting taggant is an Indocyanine Green complex.

16. The taggant composition of claim 10, wherein the Stokes-shifting taggant is an oil-dispersible taggant and is dispersed in said oil or lubricant, and optionally further comprising a surfactant or dispersant additive.

* * * * *